US006232083B1

(12) United States Patent
Fisher et al.

(10) Patent No.: US 6,232,083 B1
(45) Date of Patent: May 15, 2001

(54) METHODS AND COMPOSITIONS FOR SCREENING CLONED PROTEINS

(75) Inventors: Paul A. Fisher, Setauket; Alexander Zaika, Port Jefferson Station, both of NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/268,536

(22) Filed: Mar. 12, 1999

(51) Int. Cl.⁷ ..................................................... C12Q 1/68
(52) U.S. Cl. .......................... 435/7.1; 530/344; 549/300; 424/193.1
(58) Field of Search ........................... 530/344; 549/300; 424/193.1; 435/7.1

(56) References Cited

U.S. PATENT DOCUMENTS

| | | |
|---|---|---|
| 4,139,346 | 2/1979 | Rabbani . |
| 4,200,735 | 4/1980 | Sano et al. . |
| 4,423,158 | 12/1983 | Porath . |
| 5,045,210 | 9/1991 | Chen et al. . |
| 5,202,432 | 4/1993 | Del Campo . |
| 5,738,984 | 4/1998 | Shoseyov . |
| 5,962,641 | * 10/1999 | Nelson et al. ........................ 530/344 |
| 6,007,820 | * 10/1999 | Nag ..................................... 424/193.1 |

OTHER PUBLICATIONS

Gennaro et al "Preparation and characterization of iminodiacetic acid–cellulose filters for concentration of trace metal cations" Analytica Chimica Acta, 151 (1983) 339–347, 1983.*

El Rassi et al., "Metal Chelate–Interaction Chromatography of Proteins with Iminodiacetic Acid–Bonded Stationary Phases on Silica Support", Journal of Chromatography, 359, 241–253 (1986).

Nieba et al., "BIACORE Analysis of Histidine–Tagged Proteins Using a Chelating NTA Sensor Chip", Analytical Biochemiostry 252, 217–228 (1997).

McMahan et al., "Single–Step Synthesis and Characterization of Biotinylated Nitrilotriacetic Acid, a Unique Reagent for the Detection of Histidine–Tagged Proteins Immobilized on Nitrocellulose[1]", Analytical Biochemistry 236, 101–106 (1996).

Paborsky et al., "A Nickel Chelate Microtiter Plate Assay for Six Histidine–Containing Proteins", Analytical Biochemistry 234, 60–65 (1996).

Tao et al., "Deoxyhypusine Synthase Assay Based on the Use of Polyhistidine–Tagged Substrate and Metal Chelate–Affinity Chromatography", Analytical Biochemistry 221, 103–108 (1994).

Figueroa, et al. "High–Performance Immobilized–Metal Affinity Chromatography of Proteins on Iminodiacetic Acid Silica–Based Bonded Phases", Journal of Chromatography, 371 335–352 (1986).

Arroyo et al., *Schizsaccharomyces pombe* Proliferating Cell Nuclear Antigen Mutations Affect DNA Polymerase δ Processivity, The Journal of Biological Chemistry, vol. 271, No. 27, pp. 15971–15980 (1996).

* cited by examiner

Primary Examiner—W. Gary Jones
Assistant Examiner—Janell Taylor
(74) Attorney, Agent, or Firm—Hoffmann & Baron, LLP

(57) ABSTRACT

The present invention provides a metal charged iminodiacetic acid (IDA) cellulose for detecting a test sample having a histidine tag. The present invention also provides methods for determining cloned protein expression and function. Additionally, the present invention includes a method for the handling of denatured proteins with subsequent renaturation in situ (parenthetically after binding to metal charged IDA cellulose). A wide range of applications are contemplated for the metal charged IDA cellulose including two-dimensional high throughput screening of proteins.

59 Claims, 12 Drawing Sheets

1  2

1  2

1  2

1  2

1  2

```
      1                         21
5'-GAATTCAAGCTTGTCGACAGA -3'
3'-CTTAAGTTCGAACAGCTGTCTAGAGACGTC-5'
  30                                    1
``` colonies antibody minus pol δ complete protein stain

Western

Bypass Synthesis

METHODS AND COMPOSITIONS FOR SCREENING CLONED PROTEINS

This invention was made with government support under Grant No. ES-04068 awarded by the National Institutes of Health. The Government has certain rights in the invention.

BACKGROUND OF THE INVENTION

Screening cloned prokaryotic or eukaryotic hosts for protein expression and function is of great importance in the field of biotechnology. However, this technology requires evaluating each individual clone for protein expression and function. Often it is necessary to examine large numbers of cloned hosts to determine which expression system is most efficient or which protein has the characteristic function that is most desirable.

Mutagenesis is a powerful method for evaluating protein expression and function. Mutagenesis involves modifying one or more bases in a nucleotide sequence to express the protein of interest. However, because there are no reliable methods to predict the effect of modified nucleotide sequences, large numbers of point mutants and mutant proteins need to be individually evaluated.

In the past, screening individual mutants for protein expression and function was extremely time consuming and very labor intensive because individual samples needed to be evaluated. It was also very difficult to determine which point mutant expressed the protein of interest.

Proliferating cell nuclear antigen (PCNA) exemplifies this difficulty. Previously, the evaluation of PCNA point mutants was performed by testing individual clones for their effects in vitro on purified DNA polymerase δ (pol δ) using conventional protein identification and purification techniques of mutant PCNA molecules. This approach while effective, is very labor intensive. (See, for example, Refs. 9–11).

The isolation and purification of cloned proteins has been greatly facilitated by the use of affinity tags. A widely used affinity tag is a histidine (his) tag. These tags typically contain a string of four to ten consecutive histidine residues genetically engineered to be at either the amino- or carboxyl-terminus of recombinant proteins. Because his-tagged proteins bind to chelated metals attached to solid supports, they can easily be isolated by column chromatography with chelated metals attached to resins or beads as the solid support. Such chromatographic methods are referred to as Immobilized Metal Ion Affinity Chromatography (IMAC).

The use of IMAC for isolating proteins was first disclosed in Porath et al., (Ref. 31), wherein a resin was derivatized with iminodiacetic acid (IDA) and metal ions were chelated to the IDA-derivatized resin for immobilizing proteins. Columns with nickel-agarose or metal containing resin are typically used for isolating his-tagged proteins. The his-tagged protein binds to the matrix by interacting with the metal ions and is then eluted with a solution of imidazole, competing metal ions or salt. Unfortunately, the use of columns for detecting his-tagged proteins is very labor intensive and not amenable to high throughput screening.

An alternate method for identifying his-tagged proteins is disclosed in the QIAGEN product guide 1997. The QIAGEN method is a two dimensional method for detecting his-tagged proteins that uses Ni-nitrilotriacetic acid (Ni-NTA) attached to a column matrix to bind his-tagged proteins.

Similarly, a method for identifying his-tagged proteins on micro titter plates is disclosed in Paborsky et al., (Ref. 29). This method utilizes maleic anhydride-activated polystyrene microtiter plates coupled with N,N-bis[carboxymethyl] lysine, a derivative of nitrilotriacetic acid (NTA), to immobilized histidine-containing proteins. Paborsky also discloses a method for quantifying expression levels of the immobilized protein. These methods, although useful, are very labor intensive and not amenable to high throughput screening.

Based on the foregoing, there is still a great need for alternate methods and compositions for screening large numbers of cloned mutants for both protein expression and function. Methods and compositions that allow two-dimensional high throughput screening would be of particular value for designing proteins for pharmaceutical and industrial uses.

SUMMARY OF THE INVENTION

These and other objectives are achieved by the present invention, which in one embodiment provides a modified cellulose for detecting a protein of interest, comprising metal charged iminodiacetic acid cellulose.

In another embodiment, the present invention provides a process for preparing modified cellulose for his-tag protein binding, comprising reacting cellulose epoxide with iminodiacetic acid to form iminodiacetic acid-cellulose; and incubating the iminodiacetic acid-cellulose with a metal salt thereby preparing a metal charged iminodiacetic acid cellulose for binding his-tagged proteins.

In yet another embodiment, the present invention provides a method for screening a test sample to determine if the sample is his-tagged, comprising contacting metal charged iminodiacetic acid cellulose with the test sample; washing the iminodiacetic acid-cellulose; and detecting the his-tagged sample that remains immobilized on the metal charged iminodiacetic acid cellulose.

In one embodiment, the invention includes a method for determining protein expression, comprising introducing into cells a vector comprising a nucleic acid that encodes a protein of interest having a polyhistidine region; growing the cells that have the vector; preparing a replica of the cells that have the vector on a membrane support; expressing the protein of interest in the cells; lysing the cells on the membrane support in situ to release the protein of interest; transferring the protein of interest to a metal charged iminodiacetic acid cellulose; washing the metal charged iminodiacetic acid cellulose; and detecting the protein of interest that is immobilized on the metal charged iminodiacetic acid cellulose.

In another embodiment, the present invention includes a method for renaturing proteins, comprising denaturing a protein having a polyhistidine region; contacting the protein with metal charged iminodiacetic acid cellulose to transfer and bind the protein to the cellulose under denaturing conditions; renaturing the protein; and recovering or detecting the renatured protein.

A significant advantage of the metal charged iminodiacetic acid cellulose is that it allows for easy screening of a large number of proteins following mutagenesis. Accordingly, one skilled in the art can rapidly ascertain which mutants have desired functional activity or binding capacity.

The invention provides, for the first time, a two-dimensional screening system that is readily amenable to high throughput screening of cloned proteins. By maintaining a two-dimensional format, the present invention enables the processing of large numbers of samples concurrently. This is not possible with the three dimensional columns and gels available in the prior art.

DETAILED DESCRIPTION OF THE INVENTION

The present invention provides a novel modified cellulose for detecting a protein of interest. The modified cellulose comprises metal charged iminodiacetic acid (IDA) cellulose. The metal charged IDA cellulose of the present invention is a two-dimensional matrix that allows for high throughput screening. Examples of two dimensional matrices include paper, membranes, filters, and the like.

For purposes of the present invention, two dimensional metal charged IDA cellulose is derived generally from a sheet or membrane of cellulosic fibers. As used herein, cellulose includes any convenient, commercially available form of cellulose such as wood, pulp, cotton hemp, ramie and the like. Preferably, the cellulose is a solid matrix of cellulose acetate or paper. More preferably, a thin sheet of paper is employed, and most preferably, Whatman 3 MM paper is employed for making the metal charged IDA cellulose of the present invention.

Metal charged IDA cellulose of the present invention is charged with a metal salt. These metal salts are well recognized in the art. Preferably, the metal salts include metals which are cations that charge the IDA cellulose. These metals include nickel, zinc, iron, cobalt, cadmium, manganese and magnesium. The most preferred metal to charge IDA cellulose is $Ni^{2+}$. The structure of $Ni^{2+}$-charged IDA cellulose is shown in FIG. 1, segment 3.

In one embodiment of the present invention, the metal charged IDA cellulose is utilized to detect a protein of interest, for example, proliferating cell nuclear antigen (PCNA). Preferably, the protein of interest has a polyhistidine region or a histidine tag (his-tag). The histidine tag can be naturally occurring or provided by a vector that encodes the polyhistidine region. Typically, his-tagged proteins contain a string of at least about four to at least about ten consecutive histidine residues at either the amino (N)-terminal or carboxyl (C)-terminal end of the protein of interest. Most preferably, the protein of interest has a histidine tag of at least about four to at least about six histidine residues.

Figure 1:
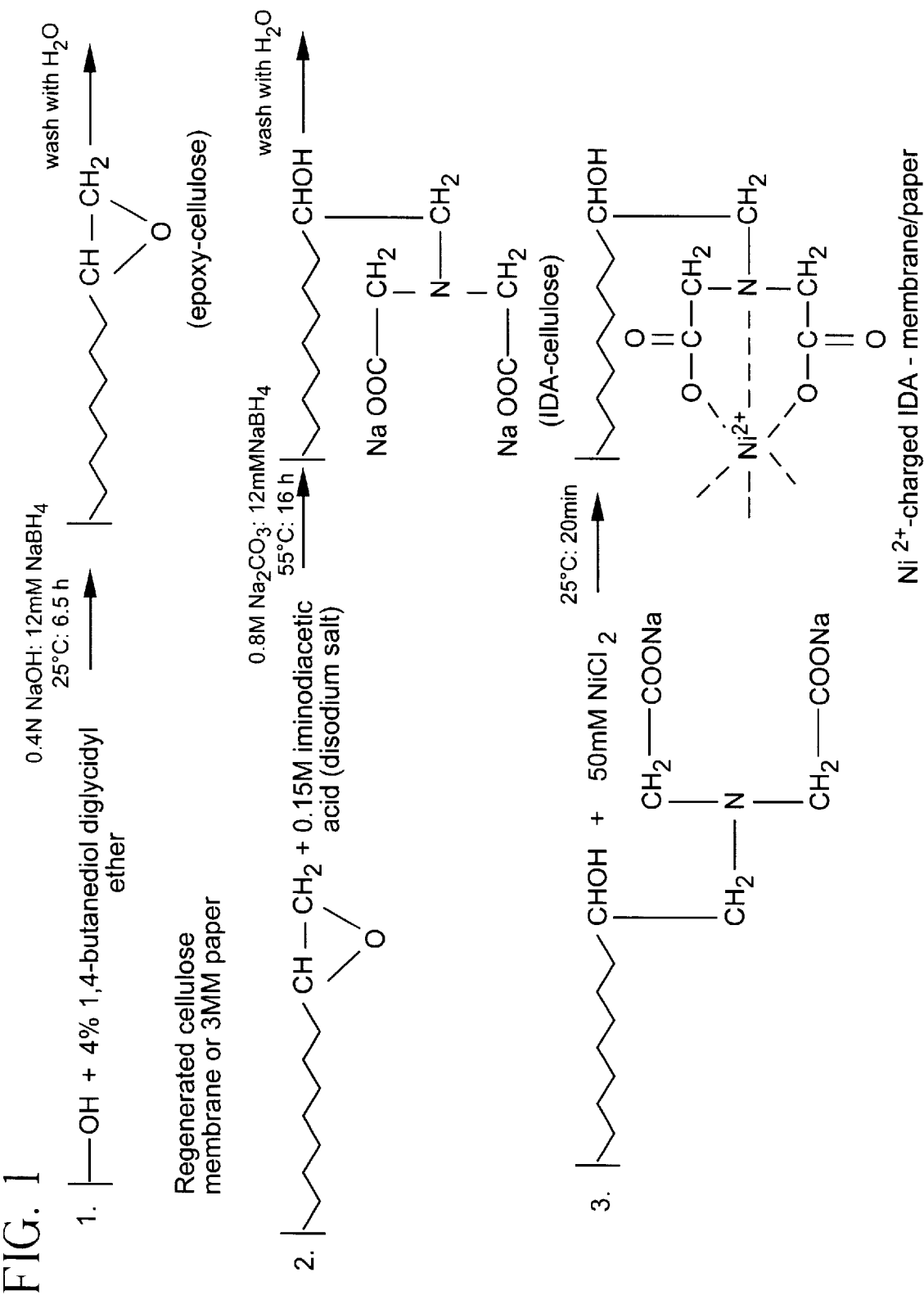
FIG. 1 is a schematic diagram showing the preparation and composition of the metal charged IDA cellulose of the present invention.

The metal charged IDA cellulose of the present invention may be prepared according to the reaction scheme shown in FIG. 1, with starting reactants known in the art. Preferably, the starting reactant is cellulose paper or cellulose acetate membrane and more preferably, Whatman 3 MM paper (shown in FIG. 1, segment 1). Preferably, the metal charged IDA cellulose is prepared by wetting the cellulose or cellulose membrane with a suitable liquid, for example, water. The wet cellulose is then contacted or reacted with an ether under basic conditions to form cellulose epoxide (epoxy-cellulose) . Most preferably, the ether used is 1,4-butanediol diglycidyl ether.

The reaction is carried out under basic conditions. As used herein, basic conditions arise upon contacting the wet cellulose with a suitable basic solution, capable of dissociating $OH^-$ ions in solution. Most Preferably, the basic conditions include a pH of about 12 or greater. An example of suitable basic solutions include combinations of $NaBH_4$, $Na_2CO_3$ and NaOH.

The cellulose-epoxide is reacted or contacted with a suitable organic acid to form iminodiacetic acid (IDA) cellulose. The reaction scheme that can be used to form IDA cellulose is shown in FIG. 1, segment 2. An example of a suitable organic acid is iminodiacetic acid. Most preferably, the concentration of iminodiacetic acid reacted with the epoxy cellulose is about 0.1M to about 0.2M.

Metal charging the iminodiacetic acid-cellulose may be accomplished by incubating the IDA cellulose with a suitable metal salt. Preferably, the metal salts include cationic metals capable of charging the IDA cellulose. These metals include nickel, zinc, iron, cobalt, cadmium, manganese and magnesium. Suitable metal salts include $NiCl_2$, $CoCl_2$, $ZnCl_2$, $MgCl_2$, and the like. Most preferably, the metal salt employed to charge IDA cellulose of the present invention is $NiCl_2$. This metal salt dissociates into $Ni^{2+}$ cations which charge the IDA cellulose. Most preferably, at least about 50 mM of $NiCl_2$ is used.

Preferably, IDA cellulose is incubated at about 25° C. with the metal salt to produce the metal charged IDA cellulose. The incubation period can vary depending on the metal salt used. Preferably, the period of incubation is at least about five minutes to at least about two hours, more preferably, at least about ten minutes to at least about one hour, and most preferably, for about ten minutes to about thirty minutes.

The amounts and concentrations of reactants used to make the metal charged IDA cellulose can vary depending on the quantity of the cellulose contacted with the reactants and the amount of metal charged IDA cellulose produced. In any event, the practitioner is guided by skill and knowledge in the field, and the present invention includes without limitation amounts of reactants which are effective to produce the metal charged IDA cellulose of the present invention.

The metal charged IDA cellulose of the present invention is useful for binding any protein or any test sample having a histidine tag. Accordingly, the present invention provides a method for screening a test sample by contacting metal charged IDA cellulose with the test sample, washing the IDA cellulose and detecting the his-tagged portion of the sample that remains immobilized on the metal charged IDA cellulose.

Examples of test samples include any macromolecule, such as proteins including isolated natural proteins, recombinantly produced or cloned proteins, a library of cloned proteins, synthetic proteins, peptides, amino acids, cell lysates, hormones, enzymes, and the like. The macromolecule can be isolated from cell lysates before applying it to the metal charged IDA cellulose. Preferably, the cell lysate is applied to wet metal charged IDA paper overlaid with a filter. A suitable filter for use with the present invention is cellulose acetate membrane.

The method of the present invention involves washing the metal charged IDA cellulose to remove contaminants and other non-his-tagged macromolecules from the metal charged IDA cellulose. Suitable agents used to wash the metal charged IDA cellulose include combinations of water, Bis-Tris, Triton X-100, NaCl, low concentrations of imidazole (such as 10 mM), glycerol and BSA (bovine serum albumin).

Metal charged IDA cellulose of the present invention immobilizes or binds macromolecules, such as proteins having histidine tags. These proteins can easily be detected or measured by various means. For example, the immobilized protein can be detected using an antibody that binds to or associates with particular region(s) of the immobilized protein. Preferably, such antibodies are monospecific. An example of a monospecific antibody used to detect his-tagged human PCNA is mAb PC10 (Oncogene Sciences, Uniondale, N.Y.). Alternately, the immobilized protein can be detected with a stain, for example, Coomassie blue or amino black.

Furthermore, once the test sample is immobilized on the metal charged IDA cellulose, qualitative or quantitative information can be provided about the test sample analyzed. For example, when the test sample derives from cloned prokaryotic or eukaryotic cells, the amount of protein expressed or produced by the particular clone can be quantified or measured. Measurement of the quantity of protein expressed can be accomplished using methods known within the art. Preferably, such measurement is conducted densitometrically to determine the protein expression level of the clone. Accordingly, the invention is highly useful for high throughput screening of a large number of mutants and cloned proteins for expression and functional activity.

Qualitatively, the functional activity of the his-tagged test sample immobilized on the metal charged IDA cellulose can be tested by functional assays using methods known by those skilled in the art. In addition, immunoassays and immunological techniques such as RIA and Western blotting can be employed.

It has been discovered that some proteins having a polyhistidine region, such as PCNA, retain biological or functional activity even after being immobilized on the metal charged IDA cellulose. For example, his-tagged PCNA, once immobilized on the metal charged IDA cellulose, is functionally active based on its ability to stimulate DNA polymerase activity in situ of purified calf thymus pol $\delta$. Accordingly, the present invention includes isolating his-tagged proteins in an active form where the isolated protein retains biological or functional activity. Examples of biological or functional activity of the protein of interest include enzyme activity or binding specificity for a particular binding site.

In another embodiment, the present invention provides a method for determining protein expression. This method includes introducing into cells a vector comprising a nucleic acid that encodes a protein of interest having a polyhistidine region. Using methodology well known in the art, nucleic acid or recombinant DNA molecules can be constructed (cDNA library) or are readily commercially available. Similarly, numerous vectors, including eukaryotic and prokaryotic vectors are commercially available to the artisan. Preferably, the vector carries a library of random point mutants with a modified nucleotide sequence that express the his-tagged protein. For example, a suitable vector for his-tagged PCNA is pQE30 which is commercially available from Qiagen, Valencia, Calif.

The vector may be introduced into the host cell by methods known in the art, such as transforming or transfecting the host cell with a live virus. The host cells can be, for example, prokaryotic cells such as *Escherichia coli*, *Staphylococcus aureus*, or eukaryotic cells such as a yeast, e.g., *Saccharomyces cerevisiae*, or cultured mammalian cells from multicellular organisms, e.g., Chinese hamster ovary cells (CHO) or Cos cells. An example of a commercially available bacterial cell line that is suitable for the present invention is *E. coli*, strain M15 from Qiagen.

Using methodology well known in the art, the transformed or transfected cells are grown to express the his-tagged protein on a suitable media such as in liquid culture, on plates or in wells. Most preferably, the transformed or transfected cells are grown in colonies on plates.

The method of the present invention is performed by transferring the protein of interest to a metal charged IDA cellulose. Preferably, the transfer of the protein of interest is accomplished using methods known in the art, such as using replica transfer from a membrane support or with a pipet. Typically, the original transformed or transfected colonies are contacted with a membrane support, such as cellulose acetate, in which case about 10% of each colony is transferred to the membrane support. The resulting cells on the membrane support are replicas or copies of the original colonies of transformed or transfected cells. These replicas are contacted with the metal charged IDA cellulose. Accordingly, a replica from each original colony is transferred to the metal charged IDA cellulose.

In an alternate embodiment, the transfected cells are lysed in situ to release intracellular proteins including the protein of interest using lysing agents well known in the art. Examples of lysing agents include lysozyme in combination with EDTA, SDS, and/or Triton X-100. Once the cells are lysed, the lysates or intracellular proteins are transferred to the metal charged IDA cellulose.

The method of the present invention includes denaturing a protein having a polyhistidine region or a histidine tag. As used herein the term "denaturing" includes treating a protein with a denaturant that results in loss of the tertiary or native structure of the protein. Denaturing conditions lead to the loss of biological or functional activity of the protein. Examples of commonly used denaturants include urea, guanidinium chloride, guanidinium thiocyanate, and detergents such as SDS.

The method of the present invention involves contacting the denatured protein with metal charged IDA cellulose to transfer and bind the protein to the cellulose under denaturing conditions. The denatured protein may be transferred to the metal charged IDA cellulose as discussed above.

Once the denatured protein is immobilized or bound to the metal charged IDA cellulose, the protein is then renatured, preferably in situ or on the metal charged IDA cellulose. As used herein, the term "renaturing" includes treating the protein with a denaturant that results in the return of the tertiary or native structure to the protein. Renaturing conditions lead to the restoration of biological activity of the protein. Examples of commonly used renaturants include urea, guanidinium thiocyanate, sodium chloride and water.

Preferably, the renaturing occurs by removing the denaturant, more preferably, by washing or diluting the denaturant, and most preferably, by diluting the denaturant with water in situ or on the metal charged IDA cellulose. In an alternate embodiment, the protein is renatured by washing the protein bound to the metal charged IDA cellulose with a denaturant of decreasing concentration. For example, if the denaturant used is 8M of urea, then the denatured protein can be renatured by washing the protein with a denaturant of decreasing concentration, for example, 6M concentration of urea to about 2M concentration of urea, until the protein renatures. Preferably, functional assays can be performed after each decreasing concentration of the denaturant is applied to the protein.

In one embodiment of the present invention, the renatured protein is recovered or eluted from the metal charged IDA cellulose using conventional methods known in the art for eluting proteins from IDA resins. For example, the protein can be eluted by washing the resin with combinations of water, Bis-Tris, Triton X-100, NaCl, high concentrations of imidazole (such as 400 mM), glycerol and BSA (bovine serum albumin).

The metal charged IDA cellulose of the present invention can be placed in wells of a manifold such as plexiglass, wood, plastic and the like. Subsequently, the test sample is placed in each well and washed, and his-tagged macromolecules are detected on the metal charged IDA cellulose. Accordingly, a large number of test samples can be screened for his-tags and the method is amenable to automation. Thus, the manipulation of each individual test sample is avoided.

The examples below are directed to the metal charged IDA cellulose of the present invention. Further examples demonstrate methods for using the metal charged IDA cellulose as a two-dimensional matrix to screen replicas of bacterial cultures or colonies after induction and cell lysis in situ for his-tagged proteins.

More particularly, using his-tagged but otherwise wild-type PCNA, an in situ assay is provided that is dependent on the ability of his-tagged PCNA to stimulate added pol δ with an exogenous template-primer. This assay was used together with random mutagenesis to identify a PCNA point-mutation that stimulates enhanced pol δ-catalyzed DNA synthesis beyond a model abasic template site. Accordingly, one of ordinary skill in the art, given the present disclosure, will understand that similar approaches may be taken to study other proteins or macromolecules that have a his-tag.

EXAMPLES

Examples have been set forth below for purpose of illustration and to describe the best mode of the invention at the present time. The scope of the invention is not to be in any way limited by the examples set forth herein.

Example 1

Materials and Methods

Much of the methodology was described (Refs. 1, 7, 8, 12–14). SDS-PAGE was according to Laemmli (Ref. 15) as modified by Fisher et al., (Ref. 16) on minigels. For immunoblots, proteins were transferred electrophoretically to nitrocellulose (Ref. 17) and resulting replicas were probed with antibodies. Reactivity was visualized colorimetrically (Ref. 18) with phosphatase-conjugated goat anti-IgG antibodies (Refs. 19, 20) and a one-solution phosphatase substrate (Kirkegaard and Perry, Gaithersburg, Md.). Immunologic detection of human PCNA was with mouse monoclonal antibody (mAb) PC10 (Oncogene Sciences, Uniondale, N.Y.). Detection of Drosophila PCNA was with affinity purified polyclonal rabbit anti-Drosophila PCNA antibodies (Ref. 12). Restriction endonucleases were from Boehringer (Indianapolis, Ind.) and were used according to the vendor's instructions. Acrylamide and methylene bis-acrylamide were from Eastman (Rochester, N.Y.) and were further purified by adsorption to an ion exchange resin. DNA sequencing performed in both directions was according to Sanger et al. (Ref. 21) using a fluorescence-based method and an ABI 373 (Applied Biosystems, Foster City, Calif.) automated DNA sequencer.

Proteins. PCNA was purified to apparent homogeneity from calf thymus (Ref. 2) as was pol δ (Refs. 14, 22). Human PCNA cDNA was cloned into a bacterial expression vector and purified from an E. coli extract (Ref. 23). D. melanogaster PCNA was purified to apparent homogeneity identically after bacterial expression (Ref. 24). Where indicated, purification of his-tagged proteins included chromatography on $Ni^{2+}$-IDA-Sepharose (Pharmacia). A his-tag was added to the $NH_2$-termini of both human and Drosophila PCNA by cDNA insertion into pQE30 (Qiagen, Valencia, Calif.) using BamH1 and HindIII restriction sites.

Nucleic Acids. Templates and primers of defined sequence were synthesized conventionally. Before use, all were purified by standard denaturing PAGE (Ref. 25). All other DNA manipulations were according to standard techniques (Ref. 25).

Example 2
Preparation of Ni$^{2+}$-charged IDA-cellulose

The procedure used to derivatize Whatman 3 MM paper is shown in FIG. 1. Before reaction, the paper was washed with H$_2$O. It was then reacted for 6.5 h at 25° C. with 4% (v/v) 1,4-butanediol diglycidyl ether in the presence of 0.4 N NaOH and 12 mM NaBH$_4$. Afterward, the resulting cellulose-epoxide was washed with H$_2$O and reacted for 16 h at 55° C. with 0.15 M IDA in the presence of 0.8 M Na$_2$CO$_3$ (unbuffered) and 12 mM NaBH$_4$. Afterward, the resulting IDA-cellulose was washed with H$_2$O and if desired, stored wet in 100 mM Tris-HCl pH 8 for up to 6 months at 4° C. Immediately before use, IDA-cellulose (washed again with H$_2$O if stored) was charged with Ni$^{2+}$ by incubation for 20 min at 25° C. with 50 mM NiCl$_2$. After charging, Ni$^{2+}$-IDA-paper was washed, first with water and then with 40 mM Bis-Tris pH 6.8, 0.01% (v/v) Triton X-100, 0.7 M NaCl, 0.1% (w/v) BSA and 10% (v/v) glycerol. By incubation with other salts (e.g., CoCl$_2$), charging with other metals can be accomplished.

In summary, FIG. 1 illustrates the chemical treatment of cellulose to immobilize his-tagged proteins. The complete treatment of either regenerated cellulose membrane or Whatman 3 MM paper to produce Ni$^{2+}$-charged IDA-cellulose is shown in segments 1–3.

Example 3
Bacterial Growth, Induction and Transfer of Proteins to Ni$^{2+}$-charged IDA-paper E. coli, strain M15 (Qiagen), were transformed with pQE30 with or without the gene encoding PCNA under control of isopropyl-β-D-thiogalactoside (IPTG). Cells were grown either as colonies on cellulose acetate membranes (0.45 μm pore size, MSI, Westboro, Mass.) laid over standard 1.5% agar plates in LB medium or in liquid culture, also in LB medium. Unmodified human PCNA under IPTG control in pT7 (Ref. 23) was maintained and induced in bacterial strain BL21(DE3). Unmodified Drosophila PCNA, also under IPTG control but in pTDT7 (Ref. 24) was maintained and induced similarly.

E. coli, strain M15 (Qiagen), were transformed with pQE30 with or without the gene encoding PCNA under control of isopropyl-β-D-thiogalactoside (IPTG). Cells were grown either as colonies on cellulose acetate membranes (0.45 μm pore size, MSI, Westboro, Mass.) laid over standard 1.5% agar plates in LB medium or in liquid culture, also in LB medium. Unmodified human PCNA under IPTG control in pT7 (Ref 23) was maintained and induced in bacterial strain BL21(DE3). Unmodified Drosophila PCNA, also under IPTG control but in pTDT7 (Ref. 24) was maintained and induced similarly.

Macromolecular transfer was performed after induction and cell lysis. For colonies, colony-containing membranes were replicated, transferred to standard agar plates containing in addition, 1 mM IPTG and induced overnight at 37° C. Induction of liquid cultures was performed by adding IPTG to a final concentration of 1 mM and continued incubation for 3 h at 37° C. Before transfer, the Ni$^{2+}$-IDA-paper was washed with lysis buffer and then kept wet with this solution. Cells were lysed by addition of a solution of 1 mg/ml of hen egg white lysozyme in "lysis buffer" (50 mM Tris-HCl pH 8, 0.1 M NaCl, 0.1% [w/v] BSA, 0.1% [v/v] Triton X-100 and 5% [v/v] glycerol); at the same time, macromolecules were transferred passively for 1 h (Ref. 16) from the cellulose acetate membrane on which colonies were grown through a similar membrane (0.45 μm pore size) which acted as an inert filter to a sheet of Ni$^{2+}$-IDA-paper placed on top of the second cellulose acetate membrane. Lysis buffer was used for transfer. Alternatively, lysate was prepared from induced cells according to standard protocols (Ref. 25) and applied directly to wet Ni$^{2+}$-IDA-paper overlaid with a cellulose acetate membrane which acted as an inert filter (i.e., lysate was applied to the Ni$^{2+}$-IDA-paper through a membrane by direct application to the membrane). After transfer, the Ni$^{2+}$-IDA-paper was washed four times, 30 min each time, each in at least 2 ml/cm$^2$ of paper. The first two washes were in 40 mM Bis-Tris pH 6.8, 0.01% (v/v) Triton X-100, 0.7 M NaCl, 0.1% (w/v) BSA, 10 mM imidazole and 10% (v/v) glycerol. The second two washes were in the same solution lacking NaCl and imidazole.

Example 4
In situ Detection of DNA Polymerase δ

Solution assays of pol δ were performed according to Ng et al. (Ref. 14). In situ assays were performed in a final volume of 30 μl/cm$^2$ of paper. Before incubation, sheets of protein-containing Ni$^{2+}$-IDA-paper were "sandwiched" between two sheets of hydrated but otherwise unmodified 3 MM paper (hydrated with solution containing 40 mM Bis-Tris pH 6.8, 6 MM MgCl$_2$, 0.1% BSA and 10% glycerol). Sheets of wet N$^{2+}$-IDA-paper prepared exactly as described above and to which macromolecules had been transferred, were placed in empty bacterial culture plates or plastic bags along with purified pol δ (0.1 μg/ml), dATP, dTTP and dCTP, each at 10 μM, 50 μCi/ml of [α-$^{32}$P]dGTP, 300 nM 21-mer DNA primer annealed to a stoichiometrically equal amount of 30-mer DNA template, 20 mM imidazole, 40 mM Bis-Tris pH 6.8, 6 mM MgCl$_2$, 0.1% BSA and 10% glycerol. Incubations followed and were at 37° C. for 180 min. Afterwards, reacted Ni$^{2+}$-IDA-paper sheets were washed extensively in solution containing 5% (w/v) trichloroacetic acid and finally subjected to analysis with a Molecular Dynamics 445 SI PhosphorImager.

Example 5
Random Mutagenesis of His-tagged Human PCNA

Random mutagenesis of human PCNA cDNA in pT7 was by polymerase chain reaction (PCR) according to Zhou et al. (Ref. 26). The primers used were 5'-AGT TAG GAT CCA TGT TCG AGG CGC GC (SEQ ID NO:1) and 5'-TCT ACA AGC TTA AGA TCC TTC TTC ATC C (SEQ ID NO:2), complementary to PCNA sequences at either end respectively, of the PCNA insert. PCR were performed in multiple 100-μl reactions for 30 cycles, each with the following temperature profile: 1.2 min at 94° C.; 1.2 min at 50° C.; 2.5 min at 72° C. About 20% of the clones contained PCNA amino acid mutations (determined empirically). After PCR, the DNA product was purified by phenol/chloroform extraction and ethanol precipitation, treated exhaustively with HindIII and BamH1, and finally purified by agarose gel electrophoresis. The restricted, purified fragment was ligated into pQE30 which had first been similarly restricted and the ligation mixture was used to transform M15 cells.

Example 6
Ni$^{2+}$-IDA-paper Binds His-tagged but not Unmodified PCNA

Figure 2A:
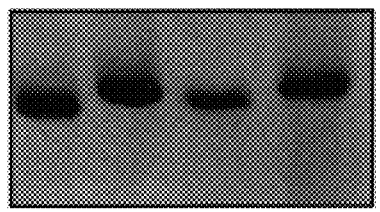
FIG. 2 shows SDS-PAGE and immunoblot analysis of bacterial expression and purification of unmodified and $NH_2$-terminally his-tagged PCNA; (A) gel was stained with Coomassie blue; (B) immunoblot probed with mAb PC10; and (C) immunoblot probed with affinity purified rabbit polyclonal anti-Drosophila PCNA antibody.

Both human and Drosophila PCNA were modified to contain NH$_2$-terminal his-tags, partially purified and compared with wild-type PCNA, similarly purified from bacterial extracts. As expected, his-tagged PCNA migrated slightly more slowly than the respective wild-type homologs during SDS-PAGE (FIG. 2A). Immunoblot analyses (FIGS. 2B and 2C) revealed that in neither case did introduction of the his-tag affect reactivity with specific antibodies.

Figure 2B:
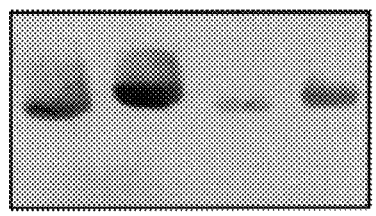
Figure 2C:
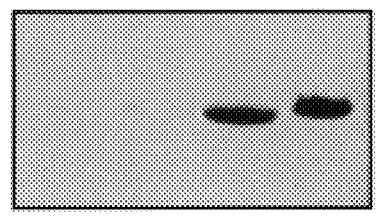

More specifically, FIG. 2 shows the results of bacterial expression and purification of unmodified and NH$_2$-terminally his-tagged PCNA; SDS-PAGE and immunoblot analysis performed. Only regions of interest are shown (FIGS. 2A–C). Referring to FIG. 2A, the gel was stained with Coomassie blue. Immunoblot analysis (shown in FIGS. 2B and 2C) of partially purified PCNA from a gel loaded and run in parallel with the one shown in FIG. 2A. Immunoblot probed with mAb PC10 is shown in FIG. 2B. Immunoblot probed with affinity purified rabbit polyclonal anti-Drosophila PCNA antibody is shown in FIG. 2C. In all panels, lanes 1 were loaded with unmodified human PCNA; lanes 2 were loaded with his-tagged human PCNA; lanes 3 were loaded with unmodified Drosophila PCNA; and lanes 4 were loaded with his-tagged Drosophila PCNA. Immunoblot analysis revealed that the introduction of the his-tag did not affect reactivity with specific antibodies.

Figure 3A:
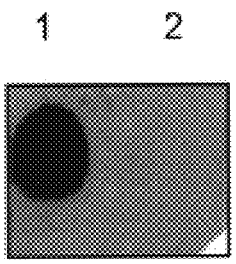
FIG. 3 shows binding of bacterial lysates containing either his-tagged (spots labeled 1) or unmodified (spots labeled 2) human PCNA; (A) binding of his-tagged PCNA to $Ni^{2+}$-IDA-paper; (B) binding of PCNA to IDA-paper (not metal charged); (C) binding of PCNA to unmodified 3MM paper; (D) binding of PCNA to $Ni^{2+}$-charged IDA-paper when incubated for 5 min in 600 mM imidazole after lysate application; and (E) binding of PCNA to nitrocellulose.
Figure 3B:
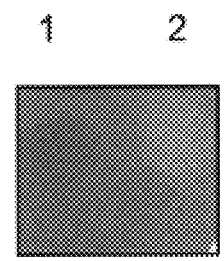
Figure 3C:
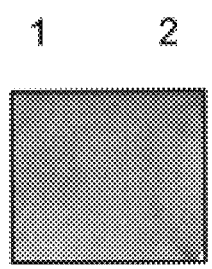
Figure 3D:
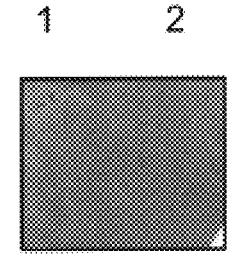
Figure 3E:
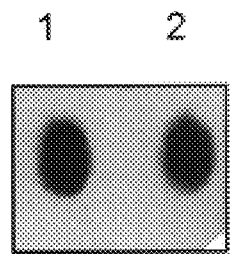

To test $Ni^{2+}$-IDA-paper, we expressed PCNA both with and without $NH_2$-terminal his-tags. Monoclonal antibodies were used to evaluate human PCNA binding after various treatments of the matrix (FIG. 3). In all cases, bacterial lysates containing either his-tagged (FIG. 3 spots labeled 1) or unmodified (FIG. 3 spots labeled 2) human PCNA, were applied directly to the two-dimensional matrix. Afterward, matrix segments were subjected to immunoblot-type analyses with mAb PC10. When $Ni^{2+}$-IDA-paper was used, only his-tagged PCNA could be detected (FIG. 3A). When IDA-paper was not charged with metal (i.e., not incubated with $NiCl_2$), little or no PCNA was detected (FIG. 3B). Similarly negative results were seen when unmodified 3 MM paper was used instead of IDA-paper (FIG. 3C) and when $Ni^{2+}$-charged IDA-paper was incubated for 5 min in 600 mM imidazole after lysate application (FIG. 3D). In contrast, binding of PCNA was readily detected when lysates were applied to nitrocellulose (FIG. 3E). PCNA binding to nitrocellulose however, was independent of the $NH_2$-terminal his-tag.

In summary, FIG. 3 illustrates binding of his-tagged and unmodified PCNA to various supports. Bacterial lysates containing equal concentrations (calibrated by SDS-PAGE and immunoblot analysis) of either his-tagged human PCNA (spots labeled 1) or unmodified human PCNA (spots labeled 2) were applied as follows: FIG. 3A, to $Ni^{2+}$-charged IDA-paper; FIG. 3B, to uncharged IDA-paper; FIG. 3C, to unmodified 3 MM paper that had first been incubated with 50 mM $NiCl_2$ as specified in FIG. 1; FIG. 3D, to $Ni^{2+}$-IDA-paper but after lysate application, it was incubated for 5 min in 600 mM imidazole; and FIG. 3E, to nitrocellulose. All were then subjected to standard immunoblot-type analysis; mAb PC10 was used as the primary and phosphatase-conjugated goat anti-mouse IgG was used as the secondary antibody. Identical results were obtained with his-tagged Drosophila PCNA versus unmodified Drosophila PCNA (not shown).

Example 6
His-tagged Human PCNA Bound to $Ni^{2+}$-IDA-paper can Stimulate Calf Thymus DNA Polymerase δ

Figure 4A:
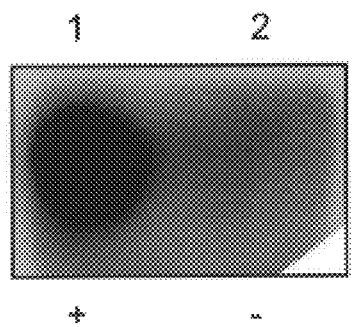
FIGS. 4(A), (B) and (C) show in situ reactivity of his-tagged human PCNA, purified calf thymus pol δ and exogenous DNA template-primer. Lysates applied to spots labeled 1 contained his-tagged human PCNA and lysates applied to spots labeled 2 contained unmodified human PCNA; (D) the nucleotide sequence of exogenous DNA template primers used in pol δ reaction; and (E) shows in situ reactivity of purified calf thymus pol δ and exogenous DNA template—primer with human PCNA but not with Drosophila PCNA.
Figure 4B:
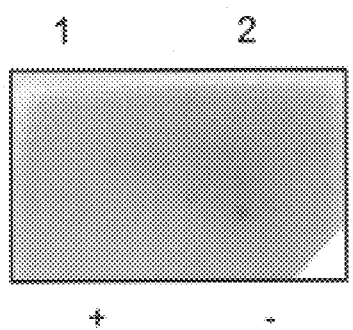
Figure 4C:
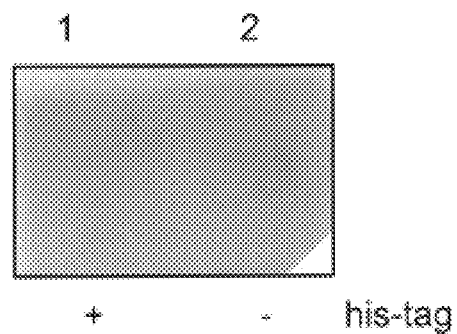

$Ni^{2+}$-IDA-paper was prepared and bacterial lysates containing either histagged (FIGS. 4A–C, spots labeled 1) or unmodified (FIGS. 4A–C, spots labeled 2) human PCNA were applied. After washing, segments were incubated with: FIG. 4A, complete DNA polymerase incubation mixture supplemented with purified calf thymus pol δ and the exogenous DNA template-primer shown in FIG. 4D; FIG. 4B, incomplete DNA polymerase incubation mixture supplemented with exogenous template-primer but lacking pol δ; or FIG. 4C, incomplete DNA polymerase incubation mixture supplemented with purified pol δ but lacking exogenous template-primer. Intense reactivity was observed, only when his-tagged, as opposed to unmodified PCNA was present in the bacterial lysate (FIG. 4A, compare spot 1 versus spot 2), and was dependent on exogenous polymerase (FIG. 4, compare panel A with panel B) as well as exogenous DNA substrate (FIG. 4, compare panel A with panel C).

Figures 4D, 4E:
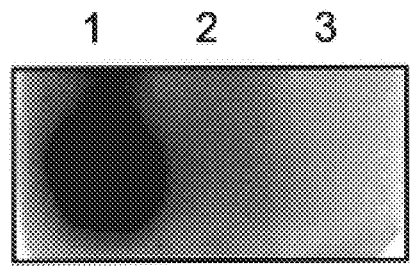

Recombinant human PCNA expressed in *E. coli* and authentic calf thymus PCNA can be used interchangeably (Refs. 8, 12, 23). In contrast, Drosophila PCNA, although 73% identical to human PCNA in primary sequence (Ref. 24) and able to substitute qualitatively for human PCNA in some contexts (Ref. 12), could only stimulate calf thymus pol δ weakly (<10% as well) (Ref. 13). Bacterial lysates containing his-tagged human PCNA, his-tagged Drosophila PCNA or lacking PCNA were applied to $Ni^{2+}$-IDA-paper. The paper was then washed and incubated in complete reaction mix including purified calf thymus pol δ and DNA template-primer (30-21-mer; see FIG. 4D). Intense reactivity was observed corresponding to the spot of human PCNA (FIG. 4E spot 1), whereas almost no reactivity was observed corresponding to the spot of Drosophila PCNA (FIG. 4E spot 2) and no reactivity was observed in the region lacking PCNA (FIG. 4E spot 3). The presence of Drosophila PCNA where applied was confirmed by standard immunoblot-type analysis with affinity purified rabbit anti-Drosophila PCNA antibodies (not shown but see FIGS. 2C and 3A).

In summary, FIG. 4 shows in situ reactivity of his-tagged human PCNA, purified calf thymus pol δ and exogenous DNA template-primer. $Ni^{2+}$-IDA-paper was prepared and washed, bacterial lysate was applied and further washing was performed, exactly as in FIG. 3. Referring to FIGS. 4A–C, lysates applied to spots labeled 1 contained his-tagged human PCNA and lysate applied to spots labeled 2 contained unmodified human PCNA. The segment shown in FIG. 4A was incubated for 180 min at 37° C. in complete polymerase reaction mix containing both purified pol δ and exogenous DNA template-primer of: 5'-GAA TTC AAG CTT GTC GAC AGA-3' (SEQ ID NO: 3) and 3'-CTT AAG TTC GAA CAG CTG TCT AGA GAC GTC-5' (SEQ ID NO: 4) as shown in FIG. 4D. These nucleotide sequences were chemically synthesized using methods known in the art (Ref. 30). The segment in FIG. 4B was incubated identically in incomplete mix lacking exogenous pol δ. The segment in FIG. 4C was incubated identically in incomplete mix lacking exogenous DNA template-primer. After incubation, all segments were washed extensively in 5% (w/v) trichloroacetic acid and subjected to PhosphorImager analysis. Referring to FIG. 4E, in situ reactivity of purified calf thymus pol δ and exogenous DNA template-primer requires his-tagged human PCNA and is not seen with his-tagged Drosophila PCNA or in the absence of PCNA. $Ni^{2+}$-IDA-paper was prepared and washed, bacterial lysate was applied and further washing was performed, exactly as in FIG. 3. The lysate applied to spot 1 contained his-tagged human PCNA. The lysate applied to spot 2 contained an equal amount of his-tagged Drosophila PCNA (calibrated by SDS-PAGE and immunoblot analysis). The lysate applied to spot 3 lacked his-tagged PCNA. After lysate application and washing, the segment shown was incubated for 180 min at 37° C. in complete mix containing both purified pol δ and exogenous DNA template-primer, washed and subjected to PhosphorImager analysis, exactly as described above.

Figure 5A:
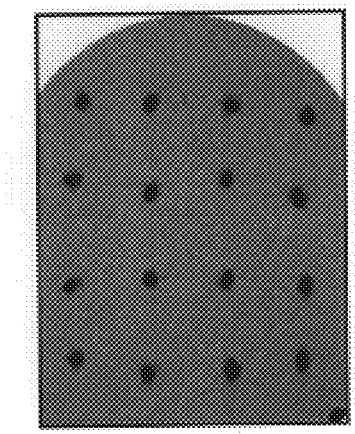
FIG. 5 shows growth of bacterial colonies, specific immobilization of histagged human PCNA on $Ni^{2+}$-IDA paper and in situ reactivity of purified calf thymus pol δ; (A) shows bacterial colonies on a cellulose acetate membrane; (B) shows $Ni^{2+}$-IDA paper after macromolecular transfer subjected to immunoblot-type analysis with mAb PC10; (C) shows $Ni^{2+}$-IDA paper after macromolecular transfer subjected to DNA polymerase analysis lacking pol δ; (D) shows $Ni^{2+}$-IDA paper after macromolecular transfer subjected to DNA polymerase analysis; and (E) shows $Ni^{2+}$-IDA paper after transfer and washing subjected to Coomassie blue staining.
Figure 5B:
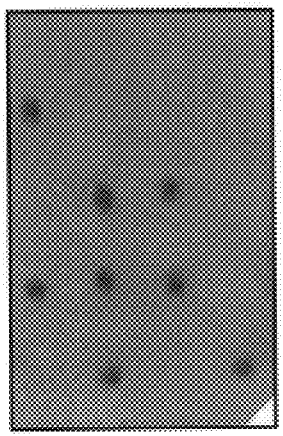
Figure 5C:
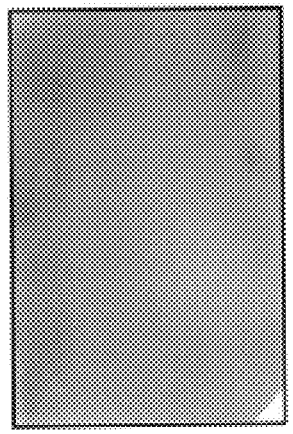
Figure 5D:
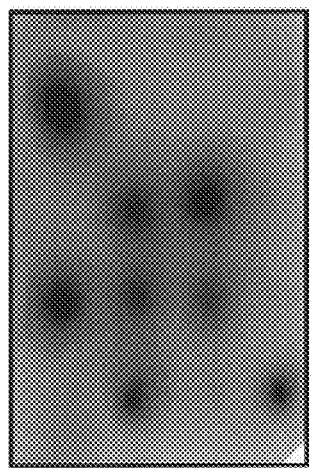

Example 7
Screening Colonies for Expression of Human PCNA Containing an $NH_2$-terminal His-tag Colonies were grown on a 0.45 μm pore size cellulose acetate membrane (FIG. 5A). All cells were transformed with IPTG-inducible plasmids but only half could express his-tagged human PCNA. The remainder contained the same plasmid but without PCNA insert. Multiple replicas were prepared. Expression was induced, colonies were lysed and proteins were transferred passively to $Ni^{2+}$-IDA-paper (Ref. 16). PCNA binding was monitored by immunoblot-type assay using mAb PC10 (FIG. 5B). In situ assay with incubation mix lacking exogenous pol δ but containing DNA template-primer (30-21-mer; see FIG. 4D) and [α-$^{32}$P]dGTP was negative (FIG. 5C). Negative results were similarly obtained when exogenous template-primer (DNA) was omitted (i.e., [α-$^{32}$P]dGTP and exogenous pol δ were both included; not shown). Hence, neither bacterial DNA polymerases, dNTP binding proteins nor DNA were adsorbed to the paper, or if present, do not produce a measurable signal in this assay. In contrast, positive results were obtained when the incubation mix contained both purified calf thymus pol δ and an exogenous template-primer. They were dependent on the presence of his-tagged human PCNA (FIG. 5D). Non-specific protein staining (Coomassie blue) failed to detect any bacterial proteins bound to the $Ni^{2+}$-IDA-paper after colony lysis and protein transfer (FIG. 5E).

In summary, FIG. 5 shows growth of bacterial colonies, specific immobilization of his-tagged human PCNA on $Ni^{2+}$-IDA-paper and in situ reactivity of purified calf thymus pol δ. Bacterial colonies were grown on 0.45 μm pore size cellulose acetate membranes. Multiple replicas were prepared. After induction and lysis, macromolecules were transferred to $Ni^{2+}$-IDA-paper. FIG. 5A shows bacterial colonies on a cellulose acetate membrane. FIG. 5B shows $Ni^{2+}$-IDA-paper after macromolecular transfer subjected to immunoblot-type analysis with mAb PC10. FIG. 5C shows $Ni^{2+}$-IDA-paper after macromolecular transfer subjected to DNA polymerase analysis with mix lacking exogenous pol δ, as in FIG. 4B. FIG. 5D shows $Ni^{2+}$-IDA-paper after macromolecular transfer subjected to DNA polymerase analysis with complete mix, as in FIG. 4A. FIG. 5E shows $Ni^{2+}$-IDA-paper after transfer and washing subjected to standard Coomassie blue staining/destaining.

Figure 5E:
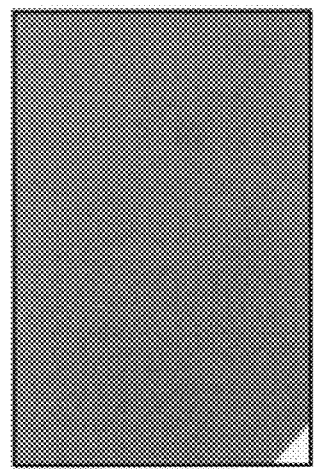
Figure 6A:
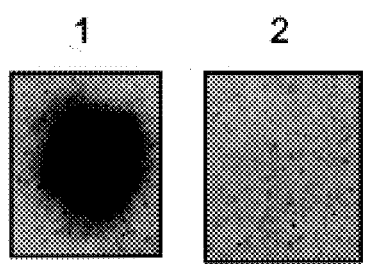
FIG. 6(A) shows Coomassie blue staining of bacterial lysates applied directly to $Ni^{2+}$-IDA-paper. The lysate applied in segment 1 contained his-tagged human PCNA. The lysate applied in segment 2 contained an equal amount of unmodified human PCNA; and (B) is a graphic illustration of densitometric quantifications of his-tagged protein binding to $Ni^{2+}$-IDA paper.

Example 8
Detectable Binding to $Ni^{2+}$-IDA-paper Depends on Expression of a His-tagged Protein Because of the small amounts of material transferred and the relative insensitivity of protein staining, colonies expressing his-tagged PCNA could not be distinguished from colonies not expressing any his-tagged protein (FIG. 5E). However, much more material could be delivered by direct application of lysates. Lysates from bacteria expressing either his-tagged or unmodified human PCNA were applied to $Ni^{2+}$-IDA-paper. Segments were washed, stained with Coomassie blue and destained. Intense staining was seen on the segment to which lysate containing histagged human PCNA was applied (FIG. 6A, panel 1). No staining was observed on the segment to which lysate containing unmodified human PCNA was applied (FIG. 6A, panel 2). Similarly, no staining was observed when solutions containing 100 mg/ml of standard proteins (either bovine serum albumin or cytochrome C, both lacking his-tags) were applied to $Ni^{2+}$-IDA-paper (not shown).

Figure 6B:
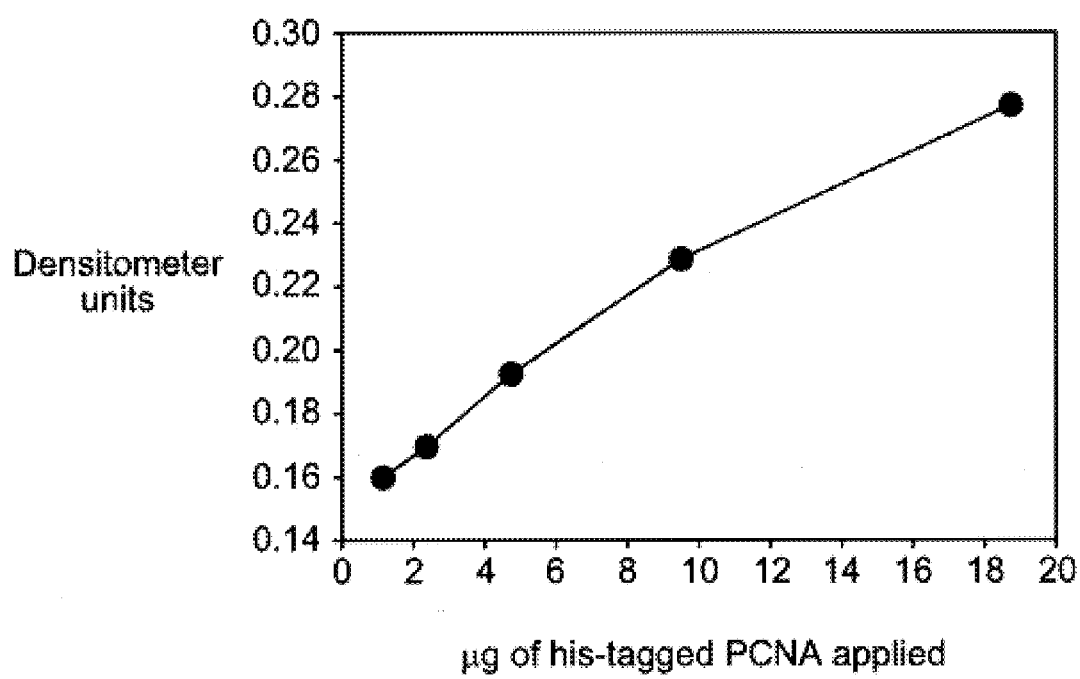

Scanning densitometry revealed that the intensity of Coomassie blue staining observed was linearly dependent on the amount of lysate containing a his-tagged protein applied to $Ni^{2+}$-IDA-paper up to a value of about 59 μg/$cm^2$ of paper (9.4 μg of singly his-tagged human PCNA applied to 0.16 square centimeters of $Ni^{2+}$-IDA-paper; FIG. 6B). Although considerably more singly his-tagged protein could be bound, some deviation from linearity was seen at higher values (FIG. 6B). Our technique therefore promises to be useful for quantifying his-tagged protein expression levels among otherwise similar transformants (or transfectants).

In summary, FIG. 6 shows Coomassie blue staining of his-tagged human but not unmodified human PCNA immobilized on $Ni^{2+}$-IDA-paper; both qualitative and quantitative analyses. FIG. 6A shows Coomassie blue staining of bacterial lysates applied directly to $Ni^{2+}$-IDA-paper. The lysate applied in panel 1 contained his-tagged human PCNA. The lysate applied in panel 2 contained an equal amount of unmodified human PCNA (calibrated by SDS-PAGE and immunoblot analysis). After washing, the segments shown were subjected to standard Coomassie blue staining/destaining. FIG. 6B shows densitometric quantification of his-tagged protein binding to $Ni^{2+}$-IDA-paper. Singly-his-tagged human PCNA was expressed in bacteria, purified to apparent homogeneity and applied in varying quantities using a plexiglas manifold to 0.16 square centimeters of $Ni^{2+}$-IDA-paper. Staining with Coomassie blue and destaining were exactly as in FIG. 6A after which, bound protein was quantified densitometrically. Plotted is the amount of protein applied (abscissa) versus the intensity of Coomassie blue staining (ordinate).

Figure 7A:
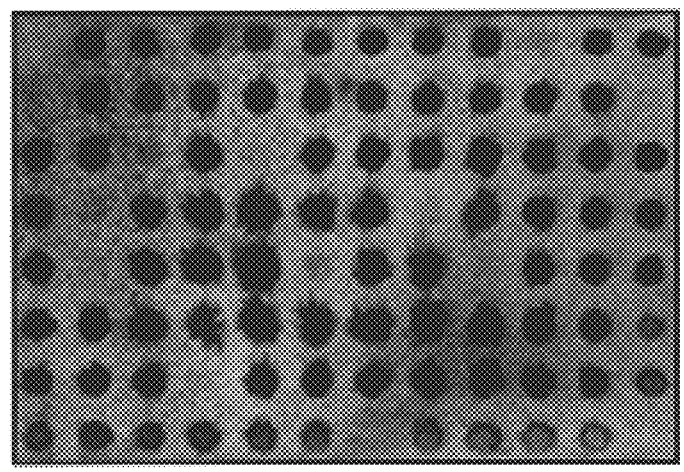
FIG. 7(A) shows Ni-IDA paper screened by immunoblot-type assay with mAb PC10; (B) shows Ni-IDA paper screened by in situ polymerase assay using a lesion-containing DNA template-primer; (C) SDS-PAGE/Coomassie blue analysis of highly purified recombinant PCNA: lane 1, unmodified wild-type human PCNA; lane 2, $NH_2$-terminally his-tagged wild-type human PCNA; lane 3, $NH_2$-terminally his-tagged $E^{85}$>K mutant human PCNA; (D) lesion-containing DNA template-primer used for the screen; (E) solution assays of pol δ in the presence and absence of different PCNA molecules: lane 1, no PCNA; lane 2, unmodified wild-type human PCNA; lane 3, $NH_2$-terminally his-tagged wild-type human PCNA; lane 4, $NH_2$-terminally his-tagged $E^{85}$>K mutant human PCNA; and (F) location of the point mutation found ($E^{85}$>K) superimposed on the crystal structure of the PCNA trimer.
Figure 7B:
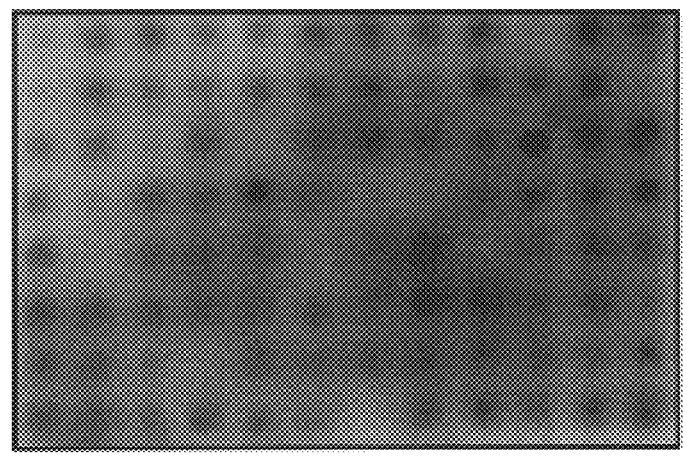
Figure 7C:
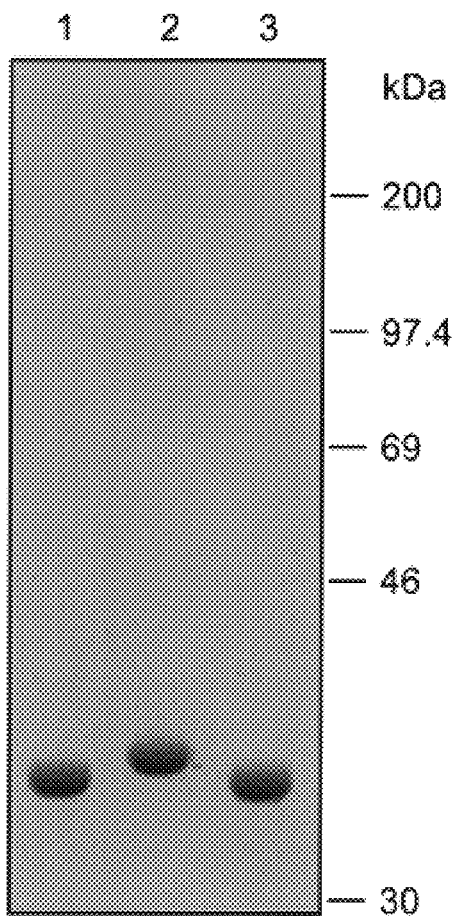
Figure 7D:
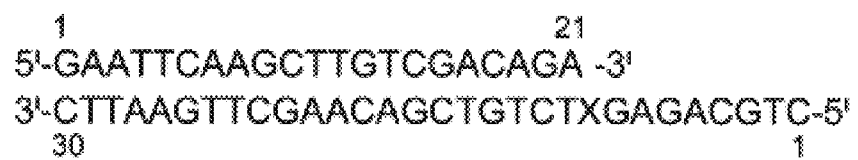

Example 9
The $E^{85}$>K PCNA Mutant; a Recombinant Molecule Identified by Screening $Ni^{2+}$-IDA-paper to which Randomly Mutagenized His-tagged PCNA was Bound To screen for mutants, the cDNA coding for PCNA was randomly mutagenized and inserted into pQE30 so as to introduce an $NH_2$-terminal his-tag. Lysates containing expressed proteins were applied to $Ni^{2+}$-IDA-paper and then screened using purified pol δ and synthetic template-primer containing a model abasic template site (FIG. 7D). To control for varying expression, a replicate filter was subjected to immunoblot-type assay with mAb PC10 (FIG. 7A). Among the first group of 96, one mutant was reproducibly detected (FIG. 7B); the mutant construct was designated pQE-mutPCNA34.

Cells harboring pQE-mutPCNA34 were grown in liquid culture, induced and mutant PCNA purified free of contaminating nuclease(s) and polymerase(s). Purification was tremendously facilitated by the his-tag. For all his-tagged proteins (including wild-type and $E^{85}$>K human PCNA; see FIG. 7C), purification included chromatography on $Ni^{2+}$-IDA-Sepharose (Pharmacia). SDS-PAGE electropherograms of purified wild-type PCNA, both without (FIG. 7C lane 1) and with (FIG. 7C lane 2) $NH_2$-terminal his-tag are shown. As expected, his-tagged PCNA moves perceptibly slower than the untagged protein. Also shown is purified protein encoded by pQE-mutPCNA34 (FIG. 7C lane 3). It too has a distinctive mobility, consistent with a single amino acid change. DNA sequencing performed in both directions indicated that the mutation is $E^{85}$>K.

Figure 7E:
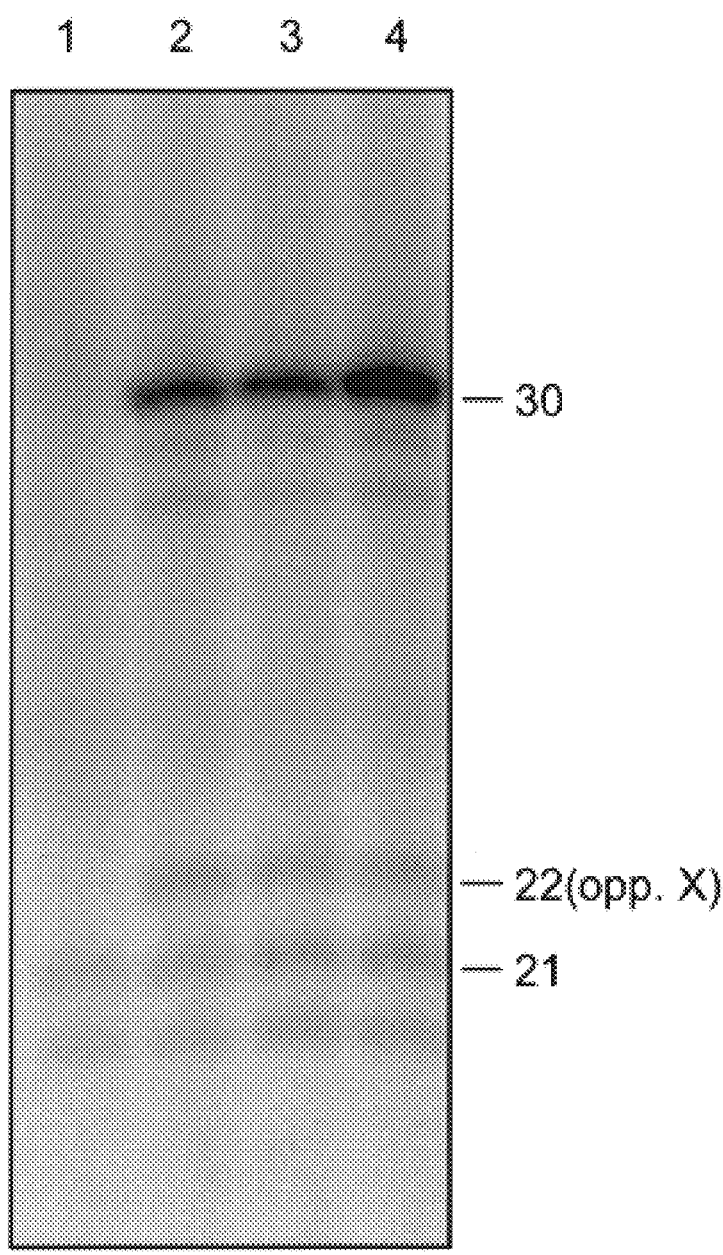

We compared $NH_2$-terminally his-tagged $E^{85}$>K mutant PCNA with wild type PCNA, both with and without $NH_2$-terminal his-tags. All stimulated purified pol δ identically on poly(dA)-oligo(dT) (not shown) but compared with wild-type, $E^{85}$>K mutant PCNA stimulated extended DNA synthesis by pol δ beyond model abasic template lesions (the original basis for screening) by about 40% as determined by PhosphorImager (FIG. 7E). Based on the crystal structure of the PCNA trimer (Ref. 27), the $E^{85}$>K mutation is on the PCNA surface thought to contact DNA (FIG. 7F), and to face away from pol δ (Ref. 28).

In summary, FIG. 7 shows the results of screening for PCNA mutants that promote extended DNA synthesis past a model abasic template site. FIG. 7A, shows Ni-IDA paper screened by immunoblot-type assay with mAb PC10. In FIG. 7B, paper was screened by in situ polymerase assay using as the only added DNA, the template-primer of: 5'-GAA TTC AAG CTT GTC GAC AGA-3' (SEQ ID NO: 3) and 3'-CTT AAG TTC GAA CAG CTG TCT XGA GAC GTC-5' (SEQ ID NO:5), shown in FIG. 7D containing a model abasic residue at the position designated X. The arrow denotes the single positive lysate from culture number 34 detected reproducibly. FIG. 7C shows SDS-PAGE/ Coomassie blue analysis of highly purified (apparently homogeneous) recombinant PCNA used for all subsequent experiments; lane 1, unmodified wild-type human PCNA; lane 2, $NH_2$-terminally his-tagged wild-type human PCNA; lane 3, $NH_2$-terminally his-tagged $E^{85}$>K mutant human PCNA. Standard proteins were subjected to SDS-PAGE simultaneously; their migration positions are indicated to the right of FIG. 7C. FIG. 7D is lesion-containing template-primer used for the screen having the nucleotide sequence of 5'-GAA TTC AAG CTT GTC GAC AGA-3' (SEQ ID NO: 3) and 3'-CTT AAG TTC GAA CAG CTG TCT XGA GAC GTC-5' (SEQ ID NO: 5) containing a model abasic residue at the position designated X. As used in the nucleotide sequence, X denotes a chemically modified sugar phosphate or a modified nucleotide without the pyrimidine or purine base. These nucleotides and sugar phosphates were chemically synthesized using procedures of Takeshita, et al., *J. Biol. Chem.* 262, (10) 171–181 (1987), the entire disclosure of which is incorporated herein by reference.

Figure 7F:
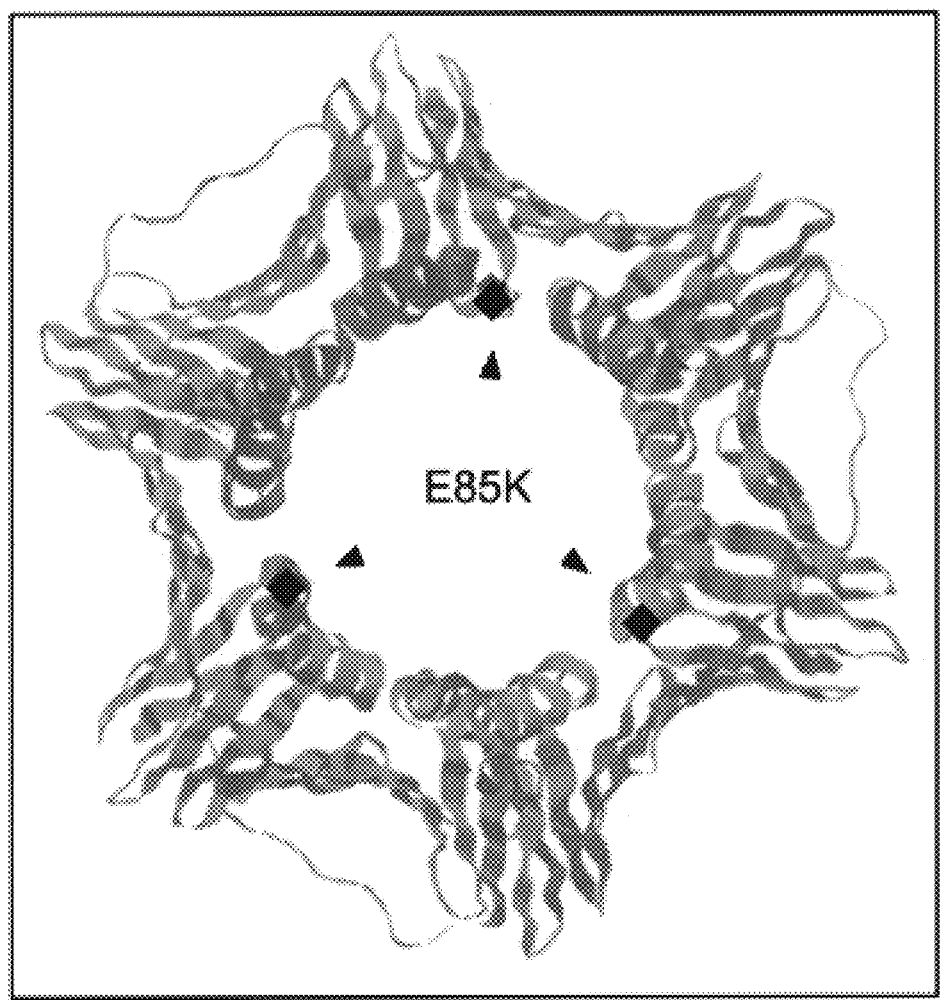

Shown in FIG. 7E are solution assays of pol δ in the presence and absence of different apparently homogeneous PCNA molecules. All reactions contained purified pol δ, dATP, dCTP, dTTP and [α-$^{32}$P]dGTP. Incubations were for 30 min at 37° C. Electrophoresis after incubation was by standard denaturing PAGE on a 16% polyacrylamide gel. The gel was subjected to routine PhosphorImager analysis. Incubations contained: lane 1, no PCNA; lane 2, unmodified wild-type human PCNA; lane 3, NH$_2$-terminally his-tagged wild-type human PCNA; lane 4, NH$_2$-terminally his-tagged $E^{85}$>K mutant human PCNA. Migration positions of the 30-mer template, the 21-mer primer and the 22-mer formed by incorporation opposite the model abasic site are shown as indicated to the right of FIG. 7E. Note that the apparent difference between the pattern seen in lanes 1 and 2 and that previously published (Ref. 8) is due to the fact that 5'-$^{32}$P-labeled 21-mer primers and unlabeled deoxyribonucleotide triphosphates were used previously, whereas present studies were performed entirely with unlabeled 21-mer primers and [α-$^{32}$P]dGTP. FIG. 7F shows location of the point mutation found ($E^{85}$>K) superimposed on the crystal structure of the PCNA trimer. The face shown is that thought to be directed away from pol δ during DNA synthesis.

The above examples clearly show the detection of protein binding to metal charged IDA paper by introducing a his-tag into that protein using genetic engineering. In addition, the present invention detects his-tagged human PCNA functionally, by its ability to stimulate the DNA polymerase activity in situ of purified calf thymus pol δ. The method of the present invention, therefore allows immediate investigation by systematic mutagenesis, of those PCNA residues important for stimulation of pol δ.

The metal charged IDA cellulose and methods of the present invention can be used for several novel applications unrelated to PCNA and/or pol δ. As discussed above, we used two-dimensional his-tagged protein immobilization and the in situ assay of pol δ to identify PCNA mutations that enhance the ability of purified calf thymus polymerase δ to replicate beyond a model abasic site. Thus far, we have found several PCNA mutants that apparently promote enhanced synthesis beyond a model abasic template site by mammalian pol δ, thereby demonstrating the utility of Ni$^{2+}$-IDA paper.

REFERENCES

1. McConnell, M., Miller, H., Mozzherin, D. J., Quamina, A., Tan, C.-K., Downey, K. M. & Fisher, P. A. (1996) *Biochemistry* 35, 8268–8274.
2. Tan, C.-K., Castilo, C., So, A. G. & Downey, K. M. (1986) *J. Biol. Chem.* 261, 12310–12326.
3. Bravo, R., Frank, R., Blundell, P. A. & Macdonald-Bravo, H. (1987) *Nature* 326, 515–517.
4. Prelich, G., Kostura, M., Marshak, D. R., Mathews, M. B. & Stillman, B. (1987) *Nature* 326, 471–475.
5. Prelich, G., Tan, C. K., Kostura, M., Mathews, M. B., So, A. G., Downey, K. M. & Stillman, B. (1987) *Nature* 326, 517–520.
6. Prelich, G. & Stillman, B. (1988) *Cell* 53, 117–126.
7. Mozzherin, D. J., McConnell, M., Jasko, M. V., Karyevsky, A. A., Tan, C.-K., Downey, K. M. & Fisher, P. A. (1996) *J. Biol. Chem.* 271, 31711–31717.
8. Mozzherin, D. J., Shirbutani, S., Tan, C.-K., Downey, K. M. & Fisher, P. A. (1997) *Proc. Natl. Acad. Sci. USA* 94, 6126–6131.
9. Fukuda, K., Morioka, H., Imajou, S., Ikeda, S., Ohtuska, E. & Tsurimoto, T. (1995) *J. Biol. Chem.* 270, 22527–22534.
10. Arroyo, M. P., Downey, K. M., So, A. G. & Wang, T.S.-F. (1996) *J. Biol. Chem.* 271, 15971–15980.
11. Zhang, P., Sun, Y., Hsu, H., Zhang, L., Zhang, Y. & Lee, M. Y. W. T. (1998) *J. Biol. Chem.* 273, 713–719.
12. Ng, L., Prelich, G., Anderson, C. W., Stillman, B. & Fisher, P. A. (1990) *J. Biol. Chem.* 265, 11948–11954.
13. Ng, L., McConnell, M., Tan, C.-K., Downey, K. M. & Fisher, P. A. (1993) *J. Biol. Chem.* 268, 13571–13576.
14. Ng, L., Tan, C.-K., Downey, K. M. & Fisher, P. A. (1991) *J. Biol. Chem.* 266, 11699–11704.
15. Laemmli, U. K. (1970) *Nature* 227, 680–685.
16. Fisher, P. A., Berrios, M. & Blobel, G. (1982) *J. Cell Biol.* 92, 674–686.
17. Harlow, E. & Lane, D. (1988) *Antibodies: a Laboratory Manual* (Cold Spring Harbor Laboratory, Cold Spring Harbor, N.Y.).
18. McGadey, J. (1970) *Histochemie* 23, 180–184.
19. Blake, M. S., Johnston, K. H., Russell-Jones, G. J. & Gotschlich, E. C. (1984) *Anal. Biochem.* 136, 175–179.
20. Smith, D. E. & Fisher, P. A. (1984) *J. Cell Biol.* 99, 20–28.
21. Sanger, F., Nicklen S. & Coulson A. R (1977) *Proc. Natl. Acad. Sci. USA* 74, 5463–5467.
22. Lee, M. Y., Tan, C.-K., Downey, K. M. & So, A. G. (1984) *Biochemistry* 23, 1906–1913.
23. Fien, K. & Stillman, B. (1992) *Mol. Cell. Biol.* 12, 155–163.
24. Yamaguchi, M., Yasuyoshi, N., Moriuchi, T., Hirose, F., Hui, C.-C., Suzuki, Y. & Matsukage, A. (1990) *Mol. Cell. Biol.* 10, 872–879.
25. Sambrook, J., Fritsch, E. F. & Maniatis, T. (1989) *Molecular Cloning: A Laboratory Manual* (Cold Spring Harbor Laboratory, Cold Spring Harbor, N.Y.).
26. Zhou, Y., Zhang, X. & Ebright, R. H. (1991) *Nucleic Acids Res.* 19, 6052.
27. Krishna, T. S., Kong, X. P., Gary, S., Burgers, P. M., Kuriyan, J. (1994) *Cell* 79, 1233–1243.
28. Jonsson, Z. O., Hindges, R., Hubscher, U. (1998) *EMBO J.* 17, 2412–2425.
29. Paborsky, L. R., Dunn, K. E., Gibbs, C. S., Dougherty, J. P. (1996) *Analytical Biochemistry* 234, 60–65.
30. Takeshita, et al., *J. Biol. Chem.* 262, (10) 171–181 (1987).
31. Porath et al., *Nature* 258:598–599 (1975).

Thus, while there have been described what are presently believed to be preferred embodiments of the present invention, those skilled in the art will realize that other and further modifications and changes can be made without departing from the true spirit of the invention, and it is intended to include all such changes and modifications as come within the scope of the invention as pointed out in the claims appended hereto.

What is claimed is:

1. A method for determining protein expression, comprising:
   (i) providing cells containing a vector comprising a nucleic acid encoding a protein of interest having a polyhistidine region, said cells expressing the protein of interest;
   (ii) transferring the protein of interest to metal charged iminodiacetic acid cellulose, immobilizing the protein of interest on the metal charged iminodiacetic acid cellulose; and (iii) detecting the protein of interest immobilized on the metal charged iminodiacetic acid cellulose.

2. The method according to claim 1, wherein the metal charged iminodiacetic acid cellulose is metal charged iminodiacetic acid cellulose paper.

3. The method according to claim 2, wherein the cells expressing the protein of interest are replicated onto a membrane support prior to transferring to the metal charged iminodiacetic acid cellulose paper.

4. The method according to claim 2, wherein the method further comprises lysing the cells to release the protein of interest before transferring the protein of interest to the metal charged iminodiacetic acid cellulose paper.

5. The method according to claim 2, wherein the protein of interest immobilized on the metal charged iminodiacetic acid cellulose paper is washed prior to detecting the protein of interest.

6. The method according to claim 1, wherein the polyhistidine region of the protein of interest is a histidine tag at the N-terminal end or at the C-terminal end.

7. The method according to claim 1, wherein the protein of interest is proliferating cell nuclear antigen (PCNA).

8. The method according to claim 1, wherein the nucleic acid vector encodes a library of random point mutations in the protein of interest.

9. The method according to claim 1, wherein the nucleic acid that encodes the protein of interest is from a cDNA library.

10. The method according to claim 1, wherein the protein of interest immobilized on the metal charged iminodiacetic acid cellulose is quantified.

11. The method according to claim 1, wherein the protein of interest immobilized on the metal charged iminodiacetic acid cellulose is quantified densitometrically.

12. The method of claim 1, wherein the metal is selected from the group consisting of nickel, zinc, iron, cobalt, cadmium, manganese and magnesium.

13. The method according to claim 1, wherein the cells containing the vector are eukaryotic cells or bacterial cells.

14. The method according to claim 13, wherein the eukaryotic cells are mammalian cells.

15. The method according to claim 14, wherein the mammalian cells are COS cells or CHO cells.

16. The method according to claim 14, wherein the mammalian cells are human cells.

17. The method according to claim 13, wherein the eukaryotic cells are yeast cells.

18. The method according to claim 13 wherein the bacterial cells are *E. coli* cells or *S. aureus* cells.

19. The method according to claim 2, wherein the following steps are inserted between steps (i) and (ii):

(a) preparing a replica of the cells that have the vector on a membrane support; and (b) lysing the replica on the membrane support in situ to release the protein of interest.

20. The method according to claim 19, further comprising a step of expressing the protein of interest in the replica, between step (a) and step (b).

21. The method according to claim 19, wherein the protein of interest immobilized on the metal charged iminoacetic acid paper in step (ii) is washed prior to detecting the protein of interest immobilized on the metal charged iminoacetic acid paper in step (iii).

22. The method according to claim 19, wherein the membrane support is cellulose acetate.

23. The method according to claim 19, wherein the protein of interest immobilized on the metal charged iminodiacetic acid cellulose is quantified.

24. The method according to claim 19, wherein the protein of interest immobilized on the metal charged iminodiacetic acid cellulose is quantified densitometrically.

25. The method according to claim 19, wherein the polyhistidine region of the protein of interest is a histidine tag at the N-terminal end or at the C-terminal end.

26. The method according to claim 19, wherein the protein of interest is proliferating cell nuclear antigen (PCNA).

27. The method according to claim 26, wherein the PCNA is human PCNA or *D. melanogaster* PCNA.

28. The method according to claim 19, wherein the nucleic acid vector encodes a library of random point mutations in the protein of interest.

29. The method according to claim 19, wherein the nucleic acid that encodes the protein of interest is from a cDNA library.

30. A method for determining a functional activity of a protein of interest, comprising:

(i) providing cells containing a vector comprising a nucleic acid encoding a protein of interest having a polyhistidine region, said cells expressing the protein of interest;

(ii) transferring the protein of interest to metal charged iminodiacetic acid cellulose, immobilizing the protein of interest on the metal charged iminodiacetic acid cellulose; and (iii) determining the functional activity the protein of interest immobilized on the metal charged iminodiacetic acid cellulose.

31. The method according to claim 30, wherein the metal charged iminodiacetic acid cellulose is metal charged iminodiacetic acid cellulose paper.

32. The method according to claim 31, wherein the cells expressing the protein of interest are replicated onto a membrane support prior to transferring to the metal charged iminodiacetic acid cellulose paper.

33. The method according to claim 31, wherein the method further comprises lysing the cells to release the protein of interest before transferring the protein of interest to the metal charged iminodiacetic acid cellulose paper.

34. The method according to claim 30, wherein the protein of interest immobilized on the metal charged iminodiacetic acid cellulose paper is washed prior to determining the functional activity of the protein of interest.

35. The method according to claim 30, wherein the polyhistidine region of the protein of interest is a histidine tag at the N-terminal end or at the C-terminal end.

36. The method according to claim 30, wherein the protein of interest is proliferating cell nuclear antigen (PCNA).

37. The method according to claim 30, wherein the nucleic acid vector encodes a library of random point mutations in the protein of interest.

38. The method according to claim 30, wherein the nucleic acid that encodes the protein of interest is from a cDNA library.

39. The method according to claim 30, wherein the functional activity of the protein of interest immobilized on the metal charged iminodiacetic acid cellulose is quantified.

40. The method according to claim 30, wherein the functional activity of the protein of interest is binding specificity, enzyme activity or stimulation of an enzyme activity.

41. The method according to claim 30, wherein the functional activity of the detected protein of interest is stimulation of δ-polymerase activity.

42. The method according to claim 30, wherein the metal is selected from the group consisting of nickel, zinc, iron, cobalt, cadmium, manganese and magnesium.

43. The method according to claim 30, wherein the cells containing the vector are eukaryotic cells or bacterial cells.

44. The method according to claim 43, wherein the eukaryotic cells are mammalian cells.

45. The method according to claim 44, wherein the mammalian cells are COS cells or CHO cells.

46. The method according to claim 44, wherein the mammalian cells are human cells.

47. The method according to claim 43, wherein the eukaryotic cells are yeast cells.

48. The method according to claim 43 wherein the bacterial cells are *E. coli* cells or *S. aureus* cells.

49. The method according to claim 31, wherein the following steps are inserted between steps (i) and (ii):
   (c) preparing a replica of the cells that have the vector on a membrane support; and
   (d) lysing the replica on the membrane support in situ to release the protein of interest.

50. The method according to claim 49, further comprising a step of expressing the protein of interest in the replica, between step (a) and step (b).

51. The method according to claim 50, wherein the protein of interest immobilized on the metal charged iminoacetic acid paper in step (ii) is washed prior to detecting the protein of interest immobilized on the metal charged iminoacetic acid paper in step (iii).

52. The method according to claim 42, wherein the membrane support is cellulose acetate.

53. The method according to claim 50, wherein the polyhistidine region of the protein of interest is a histidine tag at the N-terminal end or at the C-terminal end.

54. The method according to claim 50, wherein the protein of interest is proliferating cell nuclear antigen (PCNA).

55. The method according to claim 54, wherein the PCNA is human PCNA or *D. melanogaster* PCNA.

56. The method according to claim 49, wherein the nucleic acid vector encodes a library of random point mutations in the protein of interest.

57. The method according to claim 49, wherein the nucleic acid that encodes the protein of interest is from a cDNA library.

58. The method according to claim 49, wherein the functional activity of the detected protein of interest is binding specificity, enzyme activity or stimulation of an enzyme activity.

59. The method according to claim 58, wherein the functional activity of the detected protein of interest is stimulation of δ-polymerase activity.

* * * * *

UNITED STATES PATENT AND TRADEMARK OFFICE
CERTIFICATE OF CORRECTION

PATENT NO. : 6,232,083 B1
DATED : August 2, 2001
INVENTOR(S) : Fisher et al.

Page 1 of 1

It is certified that error appears in the above-identified patent and that said Letters Patent is hereby corrected as shown below:

Page 1, Column 2,
Line 3, now reads "Biochemiostry 252,217-228 (1997)." Should read -- Biochemistry 252, 217-228 (1997). --.
Line 20, now reads "*Schizaccharomyces pombe*" should read – *Schizzosaccharomyces pombe* --.

Column 19, claim 49,
Lines 3-6, now reads "(c) preparing a replica of the cells that have the vector on a membrane support; and
(d) lysing the replica on the membrane support in situ to release the protein of interest."
Should read – "(a) preparing a replica of the cells that have the vector on a membrane support; and
(b) lysing the replica on the membrane support in situ to release the protein of interest. ---.

Signed and Sealed this

Twenty-seventh Day of November, 2001

*Attest:*

*Attesting Officer*

NICHOLAS P. GODICI
*Acting Director of the United States Patent and Trademark Office*